United States Patent
Marion et al.

[11] Patent Number: 5,741,766
[45] Date of Patent: Apr. 21, 1998

[54] OIL-IN-WATER CLEANSING EMULSION HAVING THE APPEARANCE OF MILK

[75] Inventors: Catherine Marion, Sceaux; Nathalie Louvet-Plaisant; Liliane Lukassen, both of Chevilly-Larue, all of France

[73] Assignee: L'Oreal, Paris, France

[21] Appl. No.: 490,192

[22] Filed: Jun. 14, 1995

[30] Foreign Application Priority Data

Jun. 14, 1994 [FR] France .................................. 94 07252

[51] Int. Cl.[6] .............................. C11D 3/22; C11D 3/37; A61K 7/02; A61K 7/48
[52] U.S. Cl. .......................... 510/130; 510/136; 510/137; 510/157; 510/417; 510/410; 510/416; 510/479; 514/717; 514/844; 514/845; 514/846; 514/938
[58] Field of Search .................. 252/174.23, 174.24, 252/170, DIG. 2, DIG. 5, DIG. 13; 424/401; 514/844, 845, 777, 846, 938; 510/130, 136, 159, 137, 476, 470, 417, 479

[56] References Cited

U.S. PATENT DOCUMENTS

| | | | |
|---|---|---|---|
| 3,912,666 | 10/1975 | Spitzer et al. | 260/2.5 E |
| 4,014,995 | 3/1977 | Juliano et al. | 424/168 |
| 4,798,682 | 1/1989 | Ansmann | 252/312 |
| 4,806,262 | 2/1989 | Snyder | 252/90 |
| 5,002,680 | 3/1991 | Schmidt et al. | 252/90 |
| 5,004,598 | 4/1991 | Lochhead et al. | 424/59 |
| 5,011,681 | 4/1991 | Ciotti et al. | 424/81 |
| 5,073,371 | 12/1991 | Turner et al. | 424/401 |
| 5,073,372 | 12/1991 | Turner et al. | 424/401 |
| 5,474,775 | 12/1995 | Traitler et al. | 424/401 |
| 5,510,100 | 4/1996 | Picard et al. | 424/59 |

FOREIGN PATENT DOCUMENTS

| | | |
|---|---|---|
| 0 422 862 | 4/1991 | European Pat. Off. . |
| 0 603 078 | 6/1994 | European Pat. Off. . |
| 0 629 396 | 12/1994 | European Pat. Off. . |
| 2 668 080 | 4/1992 | France . |
| 92 06778 | 4/1992 | WIPO . |

*Primary Examiner*—Paul Lieberman
*Assistant Examiner*—Lorna M. Douyon
*Attorney, Agent, or Firm*—Oblon, Spivak, McClelland, Maier & Neustadt, P.C.

[57] ABSTRACT

Oil-in-water (O/W) cleansing emulsions having the appearance of a milk, comprising a self-emulsifiable composition based on fatty alcohols as emulsifying agent and an acrylic copolymer as gelling agent, useful for cleansing the skin of the face and/or of the body. These emulsions may be used in particular as a make-up removing milk.

5 Claims, 1 Drawing Sheet

OIL-IN-WATER CLEANSING EMULSION HAVING THE APPEARANCE OF MILK

BACKGROUND OF THE INVENTION

1. Field of the Invention

The present invention relates to an oil-in-water (O/W) cleansing emulsion having the appearance of milk, which may be used for cleansing the skin of the face and/or of the body, optionally before a cosmetic and/or dermatological treatment. In a preferred embodiment the invention emulsion may be a make-up removing milk.

The invention also relates to the use of this emulsion for deep-down cleansing of the skin and to a process for cleansing the skin.

2. Discussion of the Background

It is known that oil-in-water and water-in-oil emulsions used in the cosmetic and dermatological fields generally comprise, in order to facilitate their emulsification, emulsifying agents, especially nonionic emulsifying agents whose function is to make the fatty and aqueous phases compatible.

Depending on their consistency, these emulsions are known as "milks" for the most fluid preparations and "creams" for the firmer emulsions. Cleansing products are generally in the form of, more or less, fluid milk. The advantage of a milk is that it spreads more easily, covers dirt more easily because of its fluidity, and thus allows a more deep-down cleansing of the skin than a cream. A milk should have a texture that is fluid enough to be able to flow from a bottle and to spread well on the skin. Usually, a milk has a viscosity equal to or less than 1 Pa•s.

The emulsifying agents generally used in the preparation of emulsions contain ethylene oxide units. These emulsifying agents have the drawback, however, of being irritating. To avoid the use of these irritant emulsifying agents, the use of a self-emulsifiable composition based on fatty alcohols has been proposed in FR-A-2,668,080. However, the emulsions obtained by the use of such a composition do not make it possible to obtain a texture which is both sufficiently fluid and stable to provide a milk. While it is possible to obtain a more fluid texture by lowering the content of emulsifying agent, in the case of the self-emulsifiable composition based on fatty alcohols, this results in an unstable composition.

Furthermore, if it is desired to obtain a make-up removing milk, the introduction of a make-up removing oil into an emulsion may destabilize it, and this is especially the case in the self-emulsifiable composition based on fatty alcohols as described in FR-A-2,668,080; this results in a formulation whose stability is unsatisfactory.

There is thus a need for a stable emulsion containing a non-irritant emulsifying agent, and having the texture of a milk.

SUMMARY OF THE INVENTION

Applicant has found, surprisingly, that it is possible to obtain a stable milk by using a self-emulsifiable composition comprising fatty alcohols as emulsifying agent and an acrylic copolymer as gelling agent. The present invention is thus directed to an oil-in-water cleansing emulsion having the appearance of a milk, characterized in that it comprises a self-emulsifiable comprising fatty alcohols as emulsifying agent and an acrylic copolymer as gelling agent which overcomes the above-mentioned problems.

Another subject of the invention is the use of the emulsion defined above for cleansing the skin of the face, head, eyes and/or of the body.

Another subject of the invention is a process for cleansing the skin, comprising applying the emulsion defined above to the skin, optionally massaging the skin with the emulsion and optionally removing the emulsion with, e.g., water.

Another subject of the invention is a make-up removing milk, containing the emulsion defined above and a make-up removing oil.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
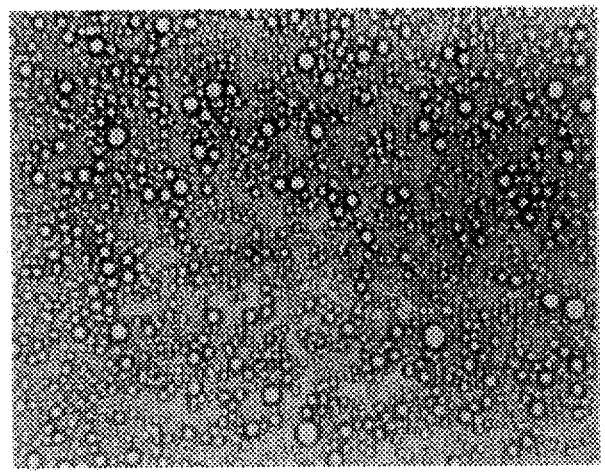
FIG. 1 is a photograph at a magnification scale of ×250 of a milk according to the present invention.

In the present invention the particular choice of an acrylic copolymer as gelling agent makes it possible to obtain an emulsion which is sufficiently fluid to constitute a milk while still having good stability, whereas other gelling agents such as, for example, polyacrylamides including the product marketed under the name Sepigel 305 by the company Seppic, do not achieve this result. Nothing would lead a person skilled in the art to choose this type of gelling agent rather than another.

The emulsion obtained according to the present invention is not only nonirritating and very stable, but also very pleasant to use, and in particular, is very soft on application. Furthermore, when it contains a make-up removing oil, it constitutes a make-up removing milk which is particularly effective and superior to the milks conventionally used. This make-up removing milk may be used both for cleansing the face and the eyes.

One acrylic copolymer which may be used in the present invention is a crosslinked copolymer of a $C_3$–$C_6$ monoethylenic acid or of the anhydride thereof with a long-chain acrylic ester. The crosslinking agent is preferably an allyl ether of glucide or of a polyol such as pentaerythritol, or with a glycol derivative such as divinyl glycol. The proportion of monoethylenic acid present in the copolymer may range from 50 to 99% by weight, preferably from 90 to 98% by weight, and the proportion of acrylic ester may range from 50 to 1% by weight, preferably from 10 to 2% by weight. All sub ranges and all values between the above ranges are included.

The monoethylenic acid may in particular be an acrylic acid of the formula:

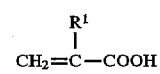

where $R_1$ represents hydrogen, halogen, hydroxyl, lactone or lactam, cyanogen, alkyl, aryl, aralkyl, alkylaryl or cycloaliphatic radicals. When $R_1$ contains carbon atoms it preferably contains from 1–22 carbon atoms. Mixtures may be used.

The monoethylenic acids preferably used for the preparation of the copolymer are acrylic acid and maleic acid and derivatives thereof.

The acrylic ester which may be used for the preparation of the invention copolymer preferably has the formula:

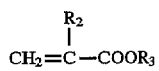

where $R_2$ represents hydrogen, methyl or ethyl radicals, and $R_3$ represents a $C_8$–$C_{30}$ alkyl, $C_8$–$C_{30}$ oxyalkylene or $C_8$–$C_{30}$ carbonyloxyalkylene radical. $C_{10}$–$C_{22}$ alkyl radicals are preferred. Among the preferred esters are the decyl, lauryl, stearyl, behenyl and melissyl acrylates and methacrylates.

The copolymer used in the present invention is preferably a copolymer of a $C_{10}$–$C_{30}$ alkyl acrylate and of acrylic or methacrylic acid, crosslinked with an allyl ether of sucrose or of pentaerythritol, and it is preferably chosen from those marketed under the names Pemulen TR1, Pemulen TR2 and Carbopol 1342 by Goodrich.

The invention copolymer may be present in amounts of from 0.02 to 0.5% by weight relative to the total weight of the emulsion, preferably from 0.05 to 0.3% by weight.

The self-emulsifiable composition used in the present invention as emulsifying agent preferably comprises from 60 to 90% by weight of at least one fatty alcohol having from 12 to 22 carbon atoms, from 10 to 40% by weight of an alkylpolyoside whose alkyl chain preferably has from 12 to 22 carbon atoms, and from 0 to 5% by weight, preferably from 0.5 to 5% by weight, of polyoside. According to a preferred embodiment of the invention, the alkyl radical of the alkylpolyoside is identical to that of the fatty alcohol of the self-emulsifiable composition.

Among the self-emulsifiable compositions which may be used in the invention, there may be mentioned those described in patent application FR-A-2,668,080, incorporated herein by reference and especially the product marketed under the name Montanov 68 by Seppic. The self-emulsifiable composition may be present in amounts ranging from 0.5 to 5% by weight relative to the total weight of the emulsion, preferably from 1 to 3.5% by weight relative to the total weight of the emulsion.

The emulsions of the invention find their application in the cleansing of the skin of the body, neck and face, eyes, etc. including for the cleansing of young children, and for the removal of make-up, including around the eyes.

The oily phase of the emulsion according to the invention comprises at least one oil which may be an animal oil, a plant oil, a mineral oil, a silicone-containing oil, a fluoro oil and/or a synthetic oil. Mixtures may be used. The oily phase of the emulsion may also contain fatty alcohols or fatty acids, and also detergents such as, for example, oxyethylenated oxypropylenated block copolymers known as poloxamers.

When the emulsion according to the invention constitutes a make-up removing milk, the oily phase also contains a make-up removing oil. As make-up removing oils, fatty acid esters, and especially esters having a total number of carbon atoms chosen between 12 and 20, in particular the esters obtained from a straight-chain or branched-chain alcohol having from 1 to 17 carbon atoms and from a straight-chain or branched-chain fatty acid having from 3 to 18 carbon atoms, are preferred. Mixtures may be used.

The esters useful as make-up removing oils may be chosen in particular from the group consisting of dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexy, 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The emulsion according to the invention preferably contains from 2 to 30% by weight of oil, more preferably from 5 to 25% by weight, including any make-up removing oil, if present, relative to the total weight of the emulsion.

The emulsion of the invention of course also contains water and may additionally contain adjuvants commonly used in the cosmetic and/or dermatological fields, such as preserving-agents, antioxidants, fragrances, fillers, screening agents, sequestering agents, essential oils, dyes, hydrophilic or lipophilic active agents, and lipid vesicles. These adjuvants are used, depending on their nature, in their usual proportions for cosmetic and/or dermatological compositions, for example from 0.01 to 10% by weight relative to the total weight of the emulsion, preferably from 0.1 to 6% by weight.

The hydrophilic or lipophilic active agents are preferably chosen from hydrating agents such as, in particular, polyols such as glycerol, and protein hydrolysates; anti-inflammatory agents, anti-free-radical agents such as tocopherol (vitamin E) or derivatives thereof; depigmenting agents; biological active agents such as urea, amino acids, vitamins and derivatives thereof, proteins, salicylic acid and derivatives thereof, α-hydroxy acids, pyrrolidonecarboxylic acid and salts thereof, ceramides and plant extracts (e.g., extract of althaea root).

The oil-in-water emulsions according to the invention are obtained according to any method, e.g., by hot-mixing, with vigorous stirring, at a temperature of about 70° C., of the oily phase containing the emulsifying agent and any lipophilic adjuvants, with the aqueous phase comprising the gelling agent and any hydrophilic adjuvants, followed by cooling to room temperature.

Other features of the invention will become apparent in the course of the following descriptions of exemplary embodiments which are given for illustration of the invention and are not intended to be limiting thereof.

EXAMPLES

In the following examples, the proportions indicated are percentages by weight.

Example 1
Make-up removing milk

| | |
|---|---|
| 2-Ethylhexyl palmitate | 20.0 |
| Sodium hydroxide (neutralizing agent) | 0.03 |
| Acrylates/$C_{10}$–$C_{30}$-alkylacrylate copolymer (Pemulen TR1 from Goodrich) | 0.1 |
| Cetearyl glucoside (Montanov 68 from Seppic) | 2.45 |
| Glycerol | 5.0 |
| Preserving agents | 0.35 |
| Water | qs 100% |

The emulsion obtained is a milk with a viscosity of 0.8 Pa·s. This milk is very soft on application and removes facial make-up very effectively.

FIG. 1 is a photograph at a magnification scale of ×250 of the emulsion obtained. It is observed in this photograph that the oil globules are homogeneous and well distributed in the aqueous phase.

The make-up removing power of this milk was tested on a panel of 49 women. 98% of these women judged it to be excellent. 90% of these users moreover found that after use of this milk, the skin remained clear, clean and non-greasy. Finally, 80% of these same women found this milk to be very soft.

Comparative Example 1
(Corresponding to Example 3 of FR-A-2,668,080)

| Cetearyl glucoside (Montanov 68) | 5.0 |
| Sweet almond oil | 5.0 |
| Polyacrylamide (Sepigel 305) (Gelling agent) | 0.3 |
| Glycerol | 5.0 |
| Preserving agent | 0.2 |
| Water | qs 100% |

The emulsion obtained constitutes a thick cream and not a milk. It a viscosity of 1.36 Pa·s and does not flow from its container. In addition, this emulsion does not remove make-up at all. It fluidized less, moistens the skin less and thus provides less effective cleansing than invention emulsions.

Figure 2:
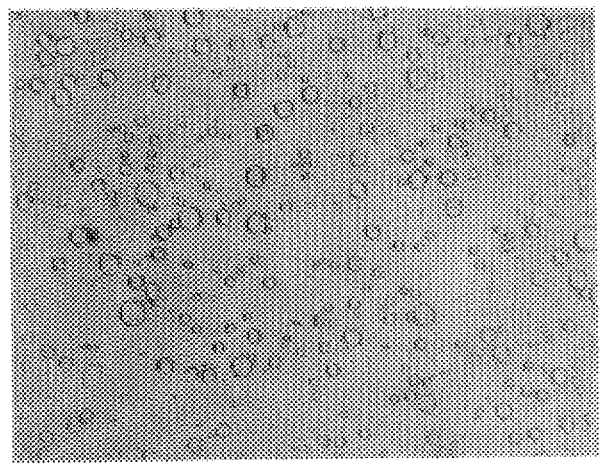
FIG. 2 is a photograph at a magnification scale of ×250 of a comparative emulsion.

FIG. 2 is a photograph at a magnification scale of ×250 of the emulsion obtained. The oil is less well dispersed than in Example 1 of the invention.

Comparative Example 2

In this example, the sweet almond oil of the above example was replaced by a make-up removing oil: 2-ethylhexyl palmitate. The composition was thus as follows:

| Cetearyl glucoside | 5.0 |
| 2-Ethylhexyl palmitate | 20.0 |
| Polyacrylamide (Sepigel 305) (Gelling agent) | 0.3 |
| Glycerol | 5.0 |
| Preserving agent | 0.2 |
| Water | qs 100% |

The emulsion obtained constitutes a thick cream and not a milk. It had a viscosity of 1.86 Pa·s and does not flow from its container. It was thus observed, when compared with Comparative Example 1, that the introduction of the make-up removing oil brought about an increase in the viscosity. Furthermore, despite the presence of the make-up removing oil, the composition obtained had a mediocre capacity to remove make-up.

Figure 3:
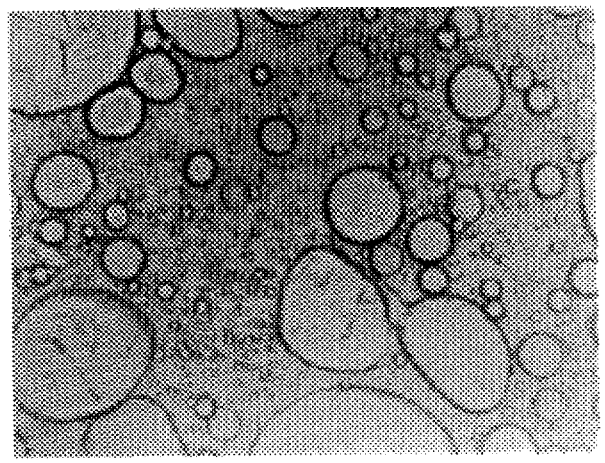
FIG. 3 is a photograph at a magnification scale of ×250 of a comparative emulsion.

Finally, this emulsion was of very coarse appearance and it is unstable, and this is seen clearly in FIG. 3 which is a photograph of the emulsion at the same scale of magnification as the above photographs. Here, the oil globules are 13 mm in size instead of 2 mm.

Example 2
baby cleansing milk

| Sweet almond oil | 7.00 |
| Liquid petrolatum | 13.00 |
| Acrylates/$C_{10}$-$C_{30}$-alkylacrylate copolymer (Pemulen TR1 from Goodrich) | 0.1 |
| Sodium hydroxide (neutralizing agent) | 0.03 |
| Cetearyl glucoside (Montanov 68 from Seppic) | 2.45 |
| Glycerol | 3.00 |
| Rose water | 3.00 |

-continued

| Preserving agents | 0.35 |
| Water | qs 100% |

The emulsion obtained constitutes a cleansing milk which is particularly gentle to use.

Example 3
softening milk for the body

| Musk rose oil | 5.00 |
| Safflower oil | 3.00 |
| Liquid petrolatum | 14.00 |
| Acrylates/$C_{10}$-$C_{30}$-alkylacrylate copolymer (Pemulen TR1 from Goodrich) | 0.10 |
| Sodium hydroxide (neutralizing agent) | 0.03 |
| Cetearyl glucoside (Montanov 68 from Seppic) | 2.45 |
| Glycerol | 5.00 |
| Extract of althaea root | 3.00 |
| Water | qs 100% |

The emulsion obtained constitutes a milk which leaves the skin feeling very soft.

Example 4
cleansing milk for the face and the eyes

| Acrylates/$C_{10}$-$C_{30}$-alkylacrylate copolymer (Pemulen TR2 from Goodrich) | 0.10 |
| Sodium hydroxide (neutralizing agent) | 0.03 |
| Cetearyl glucoside (Montanov 68 from Seppic) | 2.00 |
| Dioctyl adipate | 15.00 |
| Poloxamer 184 | 0.5 |
| Preserving agent | 0.1 |
| Water | qs 100% |

The emulsion obtained constitutes a milk which allows very effective cleansing of the face and of the eyes, and which is very gentle.

This application is based on French Patent Application 94-07252 filed on Jun. 14, 1994, which is incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An oil-in-water cleansing emulsion comprising from 0.5 to 5% by weight of a self-emulsifiable composition and 0.02 to 0.5% by weight relative to the total weight of the emulsion, of a copolymer of a $C_{10}$-$C_{30}$ alkyl acrylate and of acrylic or methacrylic acid, crosslinked with an allyl ether of sucrose or of pentaerythritol, wherein said self-emulsifiable composition comprises from 60 to 90% by weight of at least one alcohol having from 12 to 22 carbon atoms, from 10 to 40% by weight of an alkylpolyoside whose alkyl chain has from 12 to 22 carbon atoms, and from 0 to 5% by weight of polyoside, and wherein said emulsion has a viscosity equal to or less than 1 Pa·s.

2. The cleansing emulsion of claim 1, further comprising from 2 to 30% by weight of oil.

3. The cleansing emulsion of claim 1, further comprising at least one adjuvant chosen from preserving agents, antioxidants, fragrances, fillers, screening agents, sequestering agents, essential oils, dyes, hydrophilic or lipophilic active agents, and lipid vesicles.

4. A make-up removing milk, comprising the oil-in-water cleansing emulsion of claim 1, and from 2 to 30% by weight, based on the total weight of the emulsion, of a make-up removing oil.

5. A method for cleansing the skin, comprising applying to the skin the cleansing emulsion of claim 1.

* * * * *